United States Patent [19]
Beckerbauer et al.

[11] Patent Number: 5,958,822
[45] Date of Patent: Sep. 28, 1999

[54] MODIFIED FLUOROSULFONIC ACIDS

[75] Inventors: Richard Beckerbauer; Mark Andrew Harmer; Qun Sun, all of Wilmington, Del.

[73] Assignee: E. I. du Pont de Nemours and Company, Wilmington, Del.

[21] Appl. No.: 09/043,367

[22] PCT Filed: Sep. 12, 1996

[86] PCT No.: PCT/US96/14625

§ 371 Date: Mar. 16, 1998

§ 102(e) Date: Mar. 16, 1998

[87] PCT Pub. No.: WO97/11081

PCT Pub. Date: Mar. 27, 1997

Related U.S. Application Data

[60] Provisional application No. 60/005,657, Sep. 19, 1995.

[51] Int. Cl.$^6$ .............................. B01J 31/40; B01J 27/53; C07F 7/04; C07C 315/04
[52] U.S. Cl. ..................... 502/168; 502/151; 502/217; 556/428; 560/231; 568/32
[58] Field of Search ..................... 502/151, 168, 502/217; 556/428; 568/32; 560/231

[56] References Cited

U.S. PATENT DOCUMENTS

| | | | |
|---|---|---|---|
| 5,093,451 | 3/1992 | Panster et al. | 528/9 |
| 5,130,396 | 7/1992 | Panster et al. | 528/9 |
| 5,239,033 | 8/1993 | Panster et al. | 528/9 |
| 5,380,791 | 1/1995 | Panster et al. | 524/837 |

FOREIGN PATENT DOCUMENTS

| | | | |
|---|---|---|---|
| 2084967 | 6/1993 | Canada | C07F 7/08 |
| 2103653 | 2/1994 | Canada | C08G 77/27 |
| 548 821 | 6/1993 | European Pat. Off. | C07F 7/08 |
| 4 024 720 | 2/1991 | Germany | C07F 7/18 |
| WO 95/19222 | 7/1995 | WIPO | B01J 31/10 |

OTHER PUBLICATIONS

F.J. Waller et al., "Catalysis with Nafion®", Chem. Tech., 1987, 17, 438–441.
G.A. Clark et al., "Perfluorinated resin sulfonic acid (Nation®, H$^T$) Catalysis", Synthesis, 1986, 513–531.
J.S. Beck et al., "A New Family of Mesoporous Molecular Sieves Prepared with Liquid Crystal Templates", J. Am Chem. Soc., 1992, 14, 10834–10843.
G. A. Bargigia et al., "Perfluoro–w–iodo–3–oxaalkanesulfonyl fluorides as Intermediates for Surfactants and Vinyl Compounds", J. Of Fluorine Chem., 19, 403–410, 1982.
Degussa publication, "Polymers and Cataysis—The DELOXAN® Product Family", pp. 1–6.

*Primary Examiner*—Gary Geist
*Assistant Examiner*—Brian J. Davis

[57] ABSTRACT

This invention concerns modified fluorosulfonic acid compounds possessing a sulfonic acid fluoride, chloride or ester group or a sulfonic acid or a salt of a sulfonic acid group at one end and respectively a hydrolyzable or hydrolyzed silane group at the other end, said sulfonic group being adjacent a substantially fluorinated bidentate hydrocarbylene group which is in turn adjacent to a hydrocarbylene-group linked to said hydrolyzable or hydrolyzed silane group. Self-condensation of the latter compounds provides novel siloxanes and polysiloxanes. This invention further concerns novel composites comprising a metal oxide network having incorporated therein a group having the formula: $-\text{O})_q\text{Si}(\text{OH})_{n-q}\text{R}^1{}_m\text{R}^2\text{R}_f\text{SO}_3\text{Q}$, and compositions comprising a solid material having a reactive surface to which surface is attached at least one group having the formula: $-\text{O})_q\text{Si}(\text{OH})_{n-q}\text{R}^1{}_m\text{R}^2\text{R}_f\text{SO}_3\text{Q}$.

35 Claims, No Drawings

MODIFIED FLUOROSULFONIC ACIDS

This application is the national filing under 35 U.S.C. 371 of International Application No. PCT/US96/14625, filed Sep. 12, 1996, which claims the priority benefit of U.S. Provisional Application 60/005,657, filed Sep. 19, 1995.

This invention concerns compounds possessing a sulfonic acid fluoride, chloride or ester group wherein said group is adjacent to a substantially fluorinated bidentate hydrocarbylene group which is in turn adjacent to a hydrocarbylene group linked to a hydrolyzable silane group, and compounds possessing a sulfonic acid or a salt of a sulfonic acid group wherein said group is adjacent to a substantially fluorinated bidentate hydrocarbylene group which is in turn adjacent to a hydrocarbylene group linked to a hydrolyzed silane group. Siloxane derivatives, which may be oligomeric or polysiloxanes, of these latter compounds are also provided via self-condensation. Optionally, condensation can be carried out in the presence of other network forming materials to yield a network composite with hydrolyzed fluorosulfonic acid derivatives incorporated therein.

This invention further concerns novel compositions comprising a solid material bearing a reactive surface to which surface has been attached via a hydrolyzed silane group a compound possessing a sulfonic acid or a salt of a sulfonic acid group which group is adjacent to a substantially fluorinated bidentate hydrocarbylene group which is in turn adjacent to a hydrocarbylene group linked to said silane group.

BACKGROUND OF THE INVENTION

Canadian Patent Application A1 2,084,967 describes solid acid catalysts wherein a hydrocarbon chain with a pendant sulfonic acid group is bonded to a silicon. These catalysts are not of a high acid strength and at high temperatures have stability problems.

Perfluorosulfonic acid catalysts, for example perfluoropolymers containing pendant sulfonic acid groups (e.g., NAFIONO® catalyst sold by E. I. du Pont de Nemours and Company) are excellent catalysts for a wide variety of reactions. Perfluoropolymers containing pendant sulfonic acid groups are very strong acids and are used in reactions such as acylations, carbonylations, condensations, alkylations, esterifications, etherifications, hydrations, nitration, isomerizations and oligomerizations. These reactions have been reviewed extensively in "Catalysis with Nafion®", F. J. Waller, R. W. van Scoyac, Chem. Tech., 1987, 17, 438–441 and in "Perfluorinated resin sulfonic acid (Nafion® -H$^+$) Catalysis" in Synthesis, G. A. Olah, P. S. Iyer and G. K. Surya Prakasch, 1986, 513–531. A drawback to the commercial use of perfluorocarbon sulfonic acid catalysts has been their high cost and relatively low catalytic activity, for some reactions, such as alkylations in non-polar solvents.

WO95/19222 describes a solid acid microcomposite catalyst which comprises a perfluorinated ion-exchange polymer containing pendant sulfonic and/or carboxylic acid groups entrapped within and highly dispersed throughout a network of metal oxide.

EP 582879 describes shaped organosiloxane condensates, processes for their preparation and use. These organosilanes, however, are not based on perfluorosulfonic acids which are known to have higher acid strength.

The present invention provides the benefits of increased stability, reduced costs, and in some cases higher catalytic activity and improved reaction selectivity over catalysts mentioned above.

SUMMARY OF THE INVENTION

The present invention provides a compound of formula I $$X_nR^1_mSiR^2R_fSO_2Y \qquad\qquad I$$

wherein:
X is a hydrolyzable group selected from the group consisting of: halogen, alkoxy, and acyloxy;
each R$^1$ is a non-hydrolyzable group independently selected from the group consisting of: alkyl, cycloalkyl, alkenyl, cycloalkenyl, aryl and aralkyl;
n is an integer from 1 to 3, and m is an integer from 0 to 2, wherein n+m=3;
R$^2$ is a bidentate hydrocarbylene group having at least 2 carbon atoms between Si and R$_f$,
R$_f$ is a substantially fluorinated bidentate hydrocarbylene group; and
Y is fluorine, chlorine or alkoxy.

The present invention also provides a compound of formula II $$[(HO)_nR^1_mSiR^2R_fSO_3^-]_xQ_{x+} \qquad\qquad II$$

wherein:
each R$^1$ is a non-hydrolyzable group independently selected from the group consisting of: alkyl, cycloalkyl, alkenyl, cycloalkenyl, aryl and aralkyl;
n is an integer from 1 to 3, and m is an integer from 0 to 2, wherein n +m=3;
R$^2$ is a bidentate hydrocarbylene group having at least 2 carbon atoms between Si and R$_f$,
R$_f$ is a substantially fluorinated bidentate hydrocarbylene group;
Q is H, NH$_4$ or a metal ion, each Q having a valence of x; and
x is a number from 1 to 4.

The present invention further provides a siloxane or a polysiloxane comprising at least two groups, said groups being the same or different, having the formula —O)$_q$Si(OH)$_{n-q}$R$^1_m$R$^2$R$_f$SO$_3$Q, wherein R$^1$, m, n, R$^2$, R$_f$ and Q are as defined for formula II and q is 1 to n.

The present invention also provides a composite comprising a metal oxide network with at least one group having the formula $$—O)_qSi(OH)_{n-q}R^1_mR^2R_fSO_3Q,$$

wherein R$^1$, m, n, R$^2$, R$_f$ and Q are as defined formula II and q is 1 to n, incorporated within said metal oxide network.

The present invention further provides a composition comprising a solid material having a reactive surface to which surface is attached at least one group having the formula —O)$_q$Si(OH)$_{n-q}$R$^1_m$R$^2$R$_f$SO$_3$Q wherein R$^1$, m, n, R$^2$, R$_f$ and Q are as defined formula II and q is 1 to n.

DETAILED DESCRIPTION

The compounds of formula I are fluorinated compounds possessing both a hydrolyzable silane function and a sulfonic acid fluoride, chloride or ester group which compounds have the formula $$X_nR^1_mSiR^2R_fSO_2Y \qquad\qquad I$$

The compounds of formula II are fluorinated compounds possessing both a hydrolyzed silane end and a sulfonic acid or a salt of a sulfonic acid group which compounds have the formula $[(HO)_nR^1{}_mSiR^2R_fSO_3{}^-]_xQ^{x+}$  II The hydrolyzable function of formula I consists of X which is a hydrolyzable group selected from the group consisting of halogen, alkoxy, and acyloxy. Halogen includes chlorine, bromine and iodine atoms; preferably chlorine. A preferred acyloxy group is acetoxy. X is preferably $C_1$ to about $C_8$ alkoxy which can be linear or branched (e.g., ethyl hexyl alkoxy). Most preferably X is methoxy or ethoxy. In preparing the compounds of formula II from formula I, X is converted to its hydrolyzed form.

Each $R^1$ for both formula I and formula II is a non-hydrolyzable group independently selected from the group consisting of alkyl, cycloalkyl, alkenyl, cycloalkenyl, aryl and aralkyl. $R^1$ is preferably alkyl containing up to about 20 carbon atoms, and is most preferably methyl, ethyl or propyl. A preferred cycloalkyl group is cyclohexyl, preferred alkenyl groups are allyl and vinyl, a preferred aryl group is phenyl, and a preferred aralkyl group is benzyl.

For both formula I and formula II, n is an integer from 1 to 3, and m is an integer from 0 to 2, wherein n +m=3. Preferably, n is 3 and m is zero.

$R^2$ for both formula I and formula II is a linear or branched bidentate hydrocarbylene group having at least 2 carbon atoms linking Si to $R_f$. The Si and $R_f$ groups must be separated by at least two non-fluorinated carbon atoms in order to insure reasonable thermal stability. These two carbon atoms must be in a linear arrangement between the Si and $R_f$ groups. Thus, a compound having as part of its structure $—Si—CH(CH_3)—R_f—$ would not meet this requirement. By hydrocarbylene is meant a group formed by the removal of two hydrogen atoms from a hydrocarbon. Included in the definition of hydrocarbylene are arylene and alkylene such as, ethylene, propylene, butylene, pentylene, hexylene, 1,4-pentylene, 1,5-hexylene, 1,5-heptylene and the like. Thus, $R^2$ can be of the formula $—(CH_2)_k$, wherein k is an integer from 2 to 12. $R^2$ can also be a cycloalkylene group having 3 to 12 carbon atoms provided the requirement of at least 2 carbons separating Si and $R_f$ is met, or a group having the formula

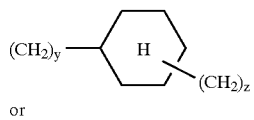

or

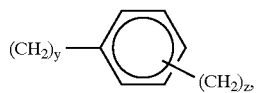

wherein each y and z are independently selected from a number 0 to 6 and denotes the number of methylene groups on the Si atom or linked to the $R_f$ group. Preferred is where $R^2$ is $—(CH_2)_k$, wherein k is an integer from 2 to 4, most preferably k is 2.

$R_f$ is a substantially fluorinated, linear or branched, bidentate hydrocarbylene group, optionally substituted by one or more ether oxygens or hydrogens. $R_f$ possesses enough fluorine to make the compound when in the sulfonic acid form a strong acid. By hydrocarbylene is meant a group formed by the removal of two hydrogen atoms from a hydrocarbon. Included in the definition of hydrocarbylene are alkylene such as, methylene, ethylene, propylene, butylene, pentylene, hexylene, 1,4-pentylene, 1,5-hexylene, 1,5-heptylene and the like. For example, $R_f$ can be $(CF_2)_{n'}$, where n' is an integer from 1 to 10; $—C(CF_3)_2—$; $CF(CF_3)$; $(CF(OR^3)CF_2)_{n''}$ where n" is an integer from 1 to 3, and $R^3$ is a perfluorocarbon of the formula $C_{n'''}F_{2n'''+}$, wherein n''' is an integer from 1 to 3. Another representative example of $R_f$ is $(CF_2)_2O(CF_2)_2$.

Y is fluorine, chlorine or an alkoxy group. Preferably the alkoxy group has 1 to 8 carbon atoms. Most preferably Y is fluorine, methoxy or ethoxy. In preparing compounds of formula II, $SO_2Y$ is converted via hydrolysis to $SO_3Q$.

Q is H, $NH_4$ or a metal ion, each Q having a valency of x=1 to 4. Representative examples of metal ions showing their valences are $Na^+$, $K^+$, $Li^+$, $Rb^+$, $Mg^{2+}$, $Ca^{2+}$, $Pt^{2+}$, and $Pd^{2+}$. Preferably Q is H or K.

In order to prepare the compounds of formula I, a vinyl derivative precursor is needed having vinyl $(CH_2=CH)$ at one end and $—R_fSO_2Y$ at the other end. This vinyl derivative precursor can be prepared, for example, in the following manner as illustrated for $X_nR^1{}_mSiR^2R_fSO_2Y$, wherein $X=OC_2H_5$; n=3; m=0; $R^2=(CH_2)_k$, wherein k is 2 or 3; $R_f$ is $(CF_2)_2O(CF_2)_2$ and Y is F:

$CF_2=CF_2 + SO_3 \rightarrow$ [tetrafluoroethanesultone] $\rightarrow FOCCF_2SO_2F$
$FOCCF_2SO_2F + CF_2=CF_2 + MF/ICl \rightarrow I(CF_2)_2O(CF_2)_2SO_2F$   1:

In 1, fluorosulfonyldifluoroacetyl fluoride $(FOCCF_2SO_2F)$ quantitatively forms from sulfur trioxide and tetrafluoroethylene (TFE) through tetrafluoro-ethanesultone. The fluorosulfonyldifluoroacetyl fluoride is subsequently converted into octafluoro-5-iodo-3-oxapentanesulfonyl fluoride $(ICF_2CF_2OCF_2CF_2SO_2F)$ by the well known reaction involving a metal fluoride (NE, such as KF), iodine and TFE in an aprotic solvent. By using the iodo compound, TFE telomers are obtained having both fluorosulfonyl and iodo terminal groups. These telomers can then be converted into the vinyl derivative precursor via two routes as shown in 2 below.

$I(CF_2)_2O(CF_2)_2SO_2F + CH_2CHCH_2OOCCH_3$
  $\rightarrow H_3CCOOCH_2CHICH_2(CF_2)_2O(CF_2)_2SO_2F$   2a:

$H_3CCOOCH_2CHICH_2(CF_2)_2O(CF_2)_2SO_2F + Zn/DMF \rightarrow$
  $CH_2=CHCH_2(CF_2)_2O(CF_2)_2SO_2F$ $I(CF_2)_2O(CF_2)_2SO_2F + CH_2=CH_2 \rightarrow ICH_2CH_2(CF_2)_2O$
  $(CF_2)_2SO_2F$   2b:

$ICH_2CH_2(CF_2)_2O(CF_2)_2SO_2F + (C_2H_5)_3N \rightarrow$
  $CH_2=CH(CF_2)_2O(CF_2)_2SO_2F$ Thus, in the case of $R^2 =(CH_2)_k$, where k=2 or 3, the vinyl derivative precursors can be made by addition of $IR_fSO_2Y$ to ethylene or allyl acetate, followed by treatment with a base or Zn (for k=3). This addition can be initiated by photo irradiation, heating, with metals or metal complexes such as Cu, Fe, Ni, Pd, Pt or $Pd(PPh_3)_4$, $Ni(PPh_3)_4$ and $RhCl(PPh_3)_3$, wherein Ph is phenyl. The base must be non- or weakly nucleophilic, such as trialkylamines, pyridine or substituted pyridines, in non-aqueous conditions.

In the case where $R^2$ is $(CH_2)k$, wherein $k \geq 4$ or other groups, the vinyl derivative precursors can be prepared by a radically initiated reaction of $IR_fSO_2Y$ with dienes or substituted dienes such as $CH_2=CHZCH=CH_2$, wherein Z is a carbon carbon double bond or is any organic stable to acid conditions and mild heating, including linear or branched or cyclic alkylene, arylene and aralkylene. The product of this reaction, $CH_2=CHZCHICH_2R_fSO_2Y$, can be reduced with a reagent such as $Be_3SNH$, Zn/Acid or $Zn/NiCl_2$.

To the vinyl derivative precursor is added a silane having a hydrolyzable group in the presence of a catalyst, such as Pt. The silane has the general formula $X_nR^1{}_mSiH$, wherein X, n, $R^1$ and m are as defined for formula I.

3:

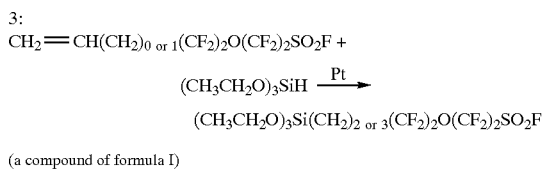

(a compound of formula I)

In order to prepare the compounds of formula II, the product of 3 above is hydrolyzed using water, an aprotic solvent, such as DMSO, and a strong base, such as KOH, in a ratio of about 60% to 30% to 10% at a temperature ranging from about 800 to 100°C. for about 10 to about 20 hours. A clear solution comprising compounds of formula II results.

4:

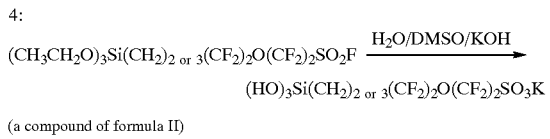

(a compound of formula II)

Self-condensation of the compounds of formula II provides siloxanes, which can be small oligomeric siloxanes or polysiloxanes, comprising at least two groups, which groups can be the same or different, having the formula $-O)_q Si(OH)_{n-q} R^1_m R^2 R_f SO_3 Q$ wherein $R^1$, m, n, $R^2$, $R_f$ and Q are as defined for formula II and q is 1 to n. For example when m=l, m=1, n=2 and q=2, the group would appear as:

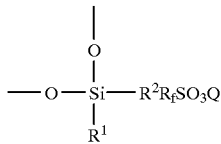

These siloxanes are derivatives of formula II wherein at least one compound of formula II is condensed with a second compound of formula II which two compounds can be the same or different and through crosslinking via oxygen bridges forms the siloxane or polysiloxane. Cross-linking can be realized simply upon adjustment of pH or even upon standing for a sufficient amount of time.

Optionally, compounds of formula II can be incorporated into a metal oxide network or a hydrous metal oxide network via co-condensation in situ with metal oxide network precursors to form a composite. For example, silicon alkoxides can be hydrolyzed and condensed, and sodium or potassium silicate solutions, and colloidal silica can be condensed to form networks. Condensation occurs via a number of routes e.g. Si—OH+Si—OH→Si—O—Si+$H_2O$. This type of condensation leads to, for example extended silica (or metal oxide). In the present invention, metal alkoxide (which may be optionally hydrolyzed) or silicate is mixed with a compound of formula II. In the case of silica, for example, a range of silicon alkoxides can be hydrolyzed and condensed to form a silica network. The compound of formula II becomes incorporated in this network. These silicon alkoxides can be represented by $Si(OR^4)_4$, where $R^4$ includes methyl, ethyl, n-propyl, iso-propyl, n-butyl, sec-butyl, iso-butyl, tert-butyl. Further metal alkoxides comprise organically modified silanes, for example $CH_3Si(OCH_3)_3$, PhSi$(OCH_3)_3$, and $(CH_3)_2 Si(OCH_3)_2$. Other representative examples of metal oxide precursors are $Si(OH)_4$, $R^5Si(OH)_3$, $R^5_2Si(OH)_2$, wherein $R^5$ is alkyl, such as methyl or ethyl; alkenyl or aryl Also included as a metal oxide network precursor is silicon tetrachloride. Other metal oxide precursors include metal silicates, for example, potassium silicate, sodium silicate, lithium silicate. K, Na or Li ions can optionally be removed using a cation exchange resin, which generates polysilicic acid which gels at slightly acid to basic pH. The use of colloidal silica and fumed silica which can be gelled by altering pH and adjusting the concentration of the colloid will also yield a network. Typical network precursors of alumina are aluminum tri-secbutoxide $Al(OC_4H_9)_3$, $Al(OH)3$, and $R^5Al(OH)_2$, wherein $R^5$ is alkyl, such as methyl or ethyl; alkenyl or aryl.

The compound of formula II can be mixed with a variety of soluble silica sources and/or metal oxide precursors, and condensation can be induced via a number of methods, for example, adjusting the pH, drying, optionally heating, and ageing for varying periods.

In 5 below, the product of 4 is co-condensed with a metal alkoxide; or alternatively, pre-hydrolyzed metal alkoxide is added. Gelation time varies from approximately 1 minute to several hours. The gel is dried, reacidified and then re-dried to form the composite of the present invention.

5:

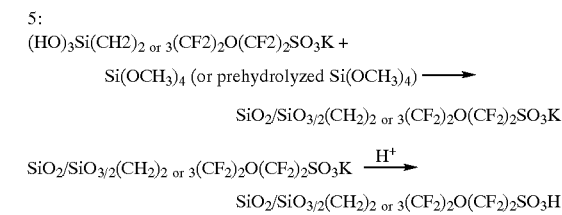

The composite, as illustrated when the metal is silicon is a porous silica (or hydrated silica) network having at least one $-O)_q Si(OH)_{n-q} R^1_m R^2 R_f SO_3 Q$ group which is believed to be sticking off of the surface of the composite. The compounds of formula II, the siloxanes and polysiloxanes and the composites of the present invention provide an advantage over known perfluorosulfonic acid catalysts in that they can be placed on a reactive surface more uniformly thus exposing a $R_f SO_3$ group making it more generally available for reaction. Known perfluorosulfonic acid catalyst usually tends to go on non-uniformly, e.g., in lumps or bits.

Certain aspects of the composite of the present invention containing the incorporated functionality of the $-O)_q Si(OH)_{n-q} R^1_m R^2 R_f SO_3 Q$ group can be varied. The pore structure can be varied by altering the pH of gelation, the drying rate, ageing the gel at higher temperatures, or varying the method of drying (drying in air, freeze drying or super-critical drying).

The siloxane, polysiloxane, composite or composition of the present invention can be spherical in shape. This is beneficial in certain applications because materials which are irregularly shaped can be subject to attrition. Attrition can lead to fines which can cause problems in certain filtering processes and columns, such as clogging, pressure build up and the generation of friction. Fines can also find their way into a final product in certain applications which is undesirable. Spherical materials can be made by incorporating the compound of formula II using an in situ sol-gel method where the compound of formula II can be mixed with a silica gel precursor, such as tetraethoxy silane or tetramethoxy silane. The precursors may be optionally hydrolyzed first or partially hydrolyzed, and gelation may be induced while stirring the material in a second immiscible solvent. Thus, a tetralkoxide could be hydrolyzed by mixing in an alcohol solvent such as ethanol with water and a catalyst and prior to gelation to a solid mass the compound of formula II could be added, followed by a mixture of water and a second phase, such as octanol. The compound of formula II and the hydrolyzed alkoxide would reside and gel in the water/alcohol phase, which is a different phase to the octanol phase. Alternatively the compound of formula II and the alkoxide could be mixed at the start and water, ethanol and a catalyst added to cause hydrolysis and condensation, the mixture left to stir and the stirrer speed could be increased (before final gelation) and a second organic phase added such as octanol, mesetylene or kerosene and the mixture stirred with optional heating to form a spherical material which can be separated by filtration. Some gelation may occur before the final addition of the second immiscible phase. Forming a gel by mixing the compound of formula II and an alkoxide or mixture of alkoxides in an emulsion will yield spherical type materials. The compound of formula II can be hydrolyzed and condensed optionally in the presence or absence of a second metal oxide or silicon oxide precursor material. Self hydrolysis and condensation in a two phase system wherein the product of hydrolysis and condensation of the compound of formula II is insoluble in the second phase leads to spherical materials. The siloxane, polysiloxane or composite can also be attached to a support which can be in a spherical or other beneficial shape, or the solid material of the compositions of the present invention can be so shaped.

Large pore zeolitic type materials referred to as mesoporous molecular sieves, have been developed which possess a regular array of uniform, near unidimensional mesopores which can be varied from 16 to 100 Å. (See J. S. Beck et al., J. Am. Chem. Soc., 1992, 114, 10834–10843). In addition to porous metal oxide networks, a group having the formula —O)$_q$Si(OH)$_{n-q}$R$^1_m$R$^2$R$_f$SO$_3$Q can also be incorporated into these sieves either in situ or reaction with the preformed material.

The present invention also provides a composition comprising a solid material having a reactive surface to which surface has been attached a compound having the formula —O)$_q$Si(OH)$_{n-q}$R$^1_m$R$^2$R$_f$SO$_3$Q, wherein R$^1$, m, n, R$^2$, R$_f$ and Q are as defined for formula II and q is 1 to n. The solid material having a reactive surface is characterized by the fact that it has some surface functionality, usually, but not necessarily, an —OH group, to which —O)$_q$Si(OH)$_{n-q}$R$^1_m$R$^2$R$_f$SO$_3$Q can attach in what is believed to be in a covalent manner via condensation. A compound of formula I is hydrolyzed to form a compound of formula II. The compound of formula II is then added to a support, the solid material having a reactive surface. Optionally, acid can be added to initiate condensation or the solution dried, or optionally heated, and the novel composition is thus formed. In this manner the —O)$_q$Si(OH)$_{n-q}$R$^1_m$R$^2$R$_f$SO$_3$Q group becomes attached through its silicon atom to the surface of the support. Attachment to the reactive surface is believed to occur in a number of ways, for example as:

—O—SiR$^1_m$R$^2$R$_f$SO$_3$Q

—O—SiR$^1_m$R$^2$R$_f$SO$_3$Q;

—O—SiR$^1_m$R$^2$R$_f$SO$_3$Q

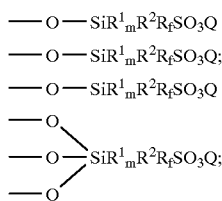

-continued

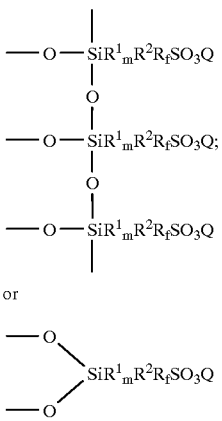

or variations thereof

Representative solid materials having a reactive surface include metal oxides. "Metal oxide" as used herein for both the compositions and composites of the present invention signifies metallic or semimetallic oxide compounds, and includes, for example alumina, silica, titania, germania, zirconia, sulfated zirconia, aluminosilicates, zirconylsilicates, chromic oxides, germanium oxides, copper oxides, molybdenum oxides, tantalum oxides, zinc copper oxides, molybdenum oxides, tantalum oxides, zinc oxides, yttrium oxides, tungsten oxides, vanadium oxides, and iron oxides. Silica is most preferred. In addition solid materials having a reactive surface also include SiC, Si$_3$N$_4$, clays, such as montmorillonite, and TiB$_2$.

The siloxanes, polysiloxanes, composites and compositions of the present invention can be porous, can display high surface area and have utility as solid acid catalysts. An advantage of the siloxanes, polysiloxanes, composites and compositions of the present invention is that few or none of the active sites (sulfonyl groups) are buried or hidden from subsequent reaction media. This represents very efficient use of the expensive sulfonyl group active sites and results in very active catalysts. The attachment of the —O)$_q$Si(OH)$_{n-q}$R$^1_m$R$^2$R$_f$SO$_3$Q group to the reactive surface in the compositions of the present invention is quite durable; it survives overnight treatment with 50% nitric acid at 80° C.

The compounds of formula II, siloxanes, polysiloxanes, composites and compositions of the present invention are useful as ion exchange materials, and as catalysts, for example, for alkylating aliphatic or aromatic hydrocarbons and nitrating organic compounds. Other commercially important applications for the compounds of formula II, siloxanes, polysiloxanes, composites and compositions of the present invention are hydrocarbon isomerization and polymerizations; olefin oligomerization; carbonylation and carboxylation reactions; hydrolysis and condensation reactions, esterifications and etherifications; hydrations and oxidations; aromatic acylation, alkylation and nitration; isomerization and metathesis reactions, and the like. Solid acid catalysts are especially useful for a range of transformations in the oil industry and for catalysis in fine chemicals, for example in the butane alkylation of butene, or in the formation of methyl tetrabutyl ether (MTBE).

Preferred uses of the compounds of formula II, siloxanes, polysiloxanes, composites and compositions described herein are in various improved processes wherein the improvement comprises using a catalytic amount of a catalyst comprising a compound of formula II, siloxane, polysiloxane, composite or composition of the present invention in place of known catalysts, such as perfluorosulfonic acids. These improved processes include the alkylation of an aromatic or substituted aromatic compound; the acylation of an aromatic or substituted aromatic compound with an acyl halide to form an aryl ketone; the oligomerization of an olefin, including substituted olefins such as styrene and α-methylstyrene; the isomerization of an olefin; and the acetic anhydride chain transfer bulk polymerization of tetrahydrofuran. Preferred catalysts for these improved processes are those wherein $R_f$ is $CF_2$ or $(CF_2)_2O(CF_2)_2$; $R^2$ is $(CH_2)k$, wherein k is 2 to 12; Q is H or K; most preferred are those wherein $R_f$ is $(CF_2)_2O(CF_2)_2$ and/or k is 2 or 3 with n=3.

In the improved process for the alkylation of an aromatic or substituted aromatic compound with an olefin, the reaction is conducted generally under normal alkylation conditions which conditions area dependent upon the reactivity of the aromatic compound and olefin used. The improvement comprises contacting the aromatic compound and the olefin in the presence of a catalytic amount of a catalyst comprising the compound of formula II, the siloxane, the polysiloxane, the composite or the composition of the present invention. Preferably the aromatic compound is toluene and the olefin is n-heptene.

In the improved process for the acylation of an aromatic or substituted aromatic compound with an acyl halide to form an aryl ketone, the reaction is conducted generally under normal acylation conditions which conditions are dependent upon the reactivity of the aromatic compound and the olefin. The improved process for the acylation of the aromatic compound with the acyl halide generally comprises heating the aromatic compound and the acyl halide and the improvement comprises the reaction proceeding in the presence of a catalytic amount of a catalyst comprising a compound of formula II, the siloxane, the polysiloxane, the composite or the composition of the present invention. After allowing sufficient time for the reaction to complete, the aryl ketone product can be recovered. Preferably the aromatic compound is m-xylene and the aryl halide is benzoyl chloride.

In the improved process for the dimerization of an α-substituted styrene, the reaction is conducted generally under normal dimerization conditions which conditions are dependent upon the reactivity of the α-substituted styrene and the improvement comprises contacting the α-substituted styrene with a catalytic amount of a catalyst comprising the compound of formula II, the siloxane, the polysiloxane, the composite, or the composition of the present invention at a temperature ranging from about −10° C. to about 100° C. Product selectivity can be varied by changing the reaction temperature. Preferably the temperature ranges from about 0° C. to about 50° C. Neat reagent or solvents can be used in the process which can be carried out in a stirred batch reactor or a fixed bed continuous flow reactor. When using cc-methylstyrene, for example, the styrene may be heated in solution and the catalyst added. The product comprises a mixture of unsaturated dimers (2,4-diphenyl-4-methyl- 1-pentene and 2,4-diphenyl4-methyl-2-pentene) and saturated dimer, 1, 1,3 -trimethyl-3-phenylidan.

In the improved process for the isomerization of an olefin, the reaction is conducted generally under normal isomerization conditions which conditions are dependent upon the reactivity of the olefin and the improvement comprises contacting the olefin with a catalytic amount of a catalyst comprising the compound of formula II, the siloxane, the polysiloxane, the composite, or the composition of the present invention. Preferred olefins have 4 to 30 carbon atoms. The olefin can be straight-chained or branched and may be a primary or secondary olefin and thus substituted with one or more groups that do not interfere with the isomerization reaction. Such substituted groups that do not interfere with the isomerization reaction could include alkyl, aryl, halide, alkoxy, esters, ethers or thioethers. Groups that may interfere with the process would be alcohols, carboxylic acids, amines, aldehydes and ketones. Preferably the olefin is 1-butene.

The present invention also provides an improved process for the polymerization of tetrahydrofuiran to polytetrahydrofuran. The product is polytetramethylene ether acetate (PTMEA), the diacetate of polytetrahydrofuran, which can be used in the preparation of "TERETHANE®" polyether glycol (a registered trademark of E. I. du Pont de Nemours and Company). A process for the polymerization of tetrahydrofuran generally comprises contacting tetrahydrofuran with acetic anhydride and acetic acid in solution usually within a pressure reactor equipped with an agitator. The reaction can be conducted at ambient temperature. The improvement herein comprises adding to the solution a catalytic amount of a catalyst comprising the compound of formula II, the siloxane, the polysiloxane, the composite, or the composition of the present invention. The reaction appears to proceed with zero order kinetics, i.e. the rate is independent of the THF concentration. The use of the present heterogeneous catalysts facilitates separating catalyst from the product. Further, the present catalysts do not appear to lose activity in repeated uses.

Catalysts comprising the compounds of formula II, siloxanes, polysiloxanes, composites and compositions of the present invention are useful in a range of catalytic reactions as described above. For some of these reactions, contaminants may form upon the catalyst or the catalyst may lose some of its activity. In some cases the used catalyst can be simply washed with water, an organic solvent or acid to remove the contaminants to recover the catalyst. In other instance, the used catalyst can be regenerated using a process which comprises contacting the used catalyst with a solution comprising an oxidizing acid an/or an oxidizing agent, such as nitric acid; and washing the oxidized catalysts with water, preferably deionized water, an organic solvent, or with both water and an organic solvent to remove any excess acid. The regeneration process can further comprise at least one of the following steps: heating the catalyst during or after contact with the oxidizing acid and/or oxidizing agent, preferably at a temperature ranging from about 15° C. to about 100° C.; isolating the oxidized catalyst via filtering, decanting or the like; and drying the catalyst, preferably at a temperature ranging from about 100° C. to about 200° C., preferably under vacuum, for a time sufficient to yield a dried regenerated catalyst, preferably about 1 hr to about 60 hrs. Each step of the regeneration process can be optionally repeated at least once.

EXAMPLES

A. Preparation of $ICH_2CH_2(CF_2)_2O(CF_2)_2{}_{SO_2}F$

A mixture of 213 g of $I(CF_2)_2O(CF_2)_2SO_2F$, 0.5 g of limonene and 30 g of ethylene was heated in an autoclave at 210° C. for 8 hours. Distillation of the resulting mixture gave 187.3 g of pure product, bp 88–89° C. at 30 mm Hg. $^{19}F$ NMR:+45.0 (t, J=5.7 Hz, 1F), −82.7 (m, 2F), −87.2 (m, 2F), −112.7 (m, 2F), −119.3 (t, J=17.0 Hz, 2F). $^1H$ NMR: 3.22 (t, J=7.8 Hz, 2H), 2.66 (m, 2H).

B. Preparation of $CH_2=CH(CF_2)_2O(CF_2)_2SO_2F$

To a stirred solution of 136.26 (0.3 mol) of $ICH_2CH_2(CF_2)_2O(CF_2)_2SO_2F$ and 200 mL of acetonitrile was slowly added 38 g (0.376 mol) of triethylamine at 75–80° C. over 6 hours. The reaction mixture was neutralized with concentrated sulfuric acid at 0° C., then poured into water and extracted with ether. The ether layer was washed with water and dried over magnesium sulfate. After removal of the ether, a residue was distilled to give 65.3 g of pure product, bp 115–117° C. $^{19}$F NMR:+45.1 (m, 1F), −82.5 (m, 2F), −87.8 (m, $_2$F), −112.5 (m, 2F), −118.0 (m, 2F). $^1$H NMR: 5.80–6.05 (m).

C. Preparation of $CH_3COOCH_2CHICH_2(CF_2)_2O(CF_2)_2SO_2F$

A mixture of 250 g of $I(CF_2)_2O(CF_2)_2SO_2F$, 77.8 g of allyl acetate and 5.2 g of copper powder in 50 mL of hexane was stirred at 90° C. for 15 hours. After removal of solids, the reaction mixture was distilled to give 234.6 g of pure product, bp 87° C. at 0.1 mmHg. $^{19}$F NMR:+45.1 (m, 1F), −82.7 (m, 2F), −87.9 (dt, J=142.4 Hz, J=13.0 Hz, 1F), −88.8 (dt, J=142.4 Hz, J=12.8 Hz, 1F), −112.7 (m, 2F), −117.3 (ddd, J=262.3 Hz, J=26.5 Hz, J=10.2 Hz, 1F), −118.6 (ddd, J=262.0 Hz, J=24.8 Hz, J=10.3 Hz, 1F). $^1$H NMR: 4.40 (m, 2H), 4.30 (m, 1H), 2.60 to 2.92 (m, 2H), 2.12 (s, 3H).

D. Preparation of $CH_2=CHCH_2(CF_2)_2O(CF_2)_2SO_2F$

To a stirred mixture of 54.4 g (0.837 mol) of zinc, 35 mL of isopropanol and 42 ml of acetic acid was slowly added 200 g (0.38 mol) of $H_3CCOOCH_2CHICH_2(CF_2)_2O(CF_2)_2SO_2F$ at 90° C. over 1 hour. The reaction mixture was stirred for 4 hours. All volatiles were then distilled out, washed with water, washed with aqueous sodium bicarbonate solution and again with water to give 117.8 g of crude product which was distilled to give 108.7 g (85% yield) of pure product, bp 134–135° C. $^{19}$F NMR:+45.0 (m, 1F), −82.6 (m, 2F), −87.3 (m, 2F), −112.6 (m, 2F), −117.4 (t, J=17.6 Hz, 2F). $^1$H NMR: 5.84–5.71 (m, 1H), 5.36–5.29 (m, 2H), 2.80 (tdt, J=17.6 Hz, J=8.0 Hz, J=1.0 Hz, 2 H).

E. Preparation of $(CH_3CH_2O)_3Si(CH_2)_3(CF_2)_2O(CF_2)_2SO_2F$

A mixture of 16.15 g (0.047 mol) of $CH_2=CHCH_2(CF_2)_2O(CF_2)_2SO_2F$, 16.27 g (0.099 mol) of $(CH_3CH_2O)_3SiH$ and three drops of platinum catalyst (Huls PC 072) was heated to 140° C. for 6 hr. A slight amount of oxygen was introduced to the reaction mixture during this 6 hour period. After cooling and stirring at 25° C. for 16 hr., the mixture was distilled under vacuum to yield 20.37 g (86% yield) of pure $(CH_3CH_2O)_3Si(CH_2)_3(CF_2)_2O(CF_2)_2SO_2F$ as a colorless liquid (bp 110–124° C. at 5 mm Hg). $^1$H NMR $(C_6D_6)$ 0.51 (t, 2H, $CH_2Si$), 1.13 (t, 9H, $CH_3$), 1.66–2.01 (m, 4H, $CH_2CH_2$), 3.71 (q, 6H, $CH_2O$). $^1$C NMR $(C_6D_6)$ 10.86 $(SiCH_2)$, 15.05 $(CH_2)$, 18.18 $(CH_3)$, 33.54 (t, $CH_2CF_2$, $^2J_{(CF)}$=21.6 Hz), 58.94 $(OCH_2)$, 108–123, (m, $CF_2$). MS (EI) m/e 503 (M$^+$—HO, 489 (M$^+$—H), 489 (M$^+$—$CH_3$), 459 (M$^+$—$OCH_2CH_3$); exact mass for M$^+$—H fragment, $C_{13}H_{20}SO_6F_9Si$, calc'd m/e 503.06061803, found m/e 503.060178.

F. Preparation of $(CF_3CH_2O)_3Si(CH_2)_2(CF_2)_2O(CF_2)_2SO_2F$

A mixture of 11.99 g of (0.037 mol) of $CH_2=CH(CF_2)_2O(CF_2)_2SO_2F$, 13.23 g (0.041 mol) of $(CF_3CH_2O)_3SiH$ and five drops of platinum catalyst (Huls PC 072) was heated to 80° C. for 4 hr. After cooling and stirring at 25° C. for 16 hr., the mixture was distilled under vacuum to yield 8.94 g (37% yield of pure $(CF_3CH_2O)_3Si(CH_2)_2(CF_2)_2O(CF_2)_2SO_2F$ as a colorless liquid (bp 134–142° C. at 40 mm Hg). Another fraction consisting of 10.7 g (44% yield) of product was also obtained. $^1$H NMR$(C_6D_6)$ 0.42–0.53 (m, 2H, $CH_2Si$), 1.91–2.13 (m, 2H, $CH_2CF_2$), 3.53 (q, 6H, $CH_2CF_3$). $^1$C NMR $(C_6D_6)$ 0.66 $(SiCH_2)$, 24.35 (t, $CH_2CF_2^2$, $J_{(CF)}$=23.3 Hz), 61.67, (q, $CH_2CF_3$, $^2J_{(CF)}$=36.8 Hz), 124.2 (q, $CF_3$, $^1J_{(CF)}$=277.9 Hz). K$^+$IDS MS m/e 503 (M$^+$=39, 100%).

Example 1

5 g of $(CH_3CH_2O)_3Si(CH_2)_3(CF_2)_2O(CF_2)_2SO_2F$ was added to 20 ml of a mixture of distilled water/DMSO/KOH (58% water/30% DMSO/12% KOH) in a round bottom flask with a reflux condenser attached. The initial mixture of the two immiscible liquids was heated at 90° C. for 18 hours by which time a clear solution had formed. The solution was left to cool. This solution will be referred to as solution 1 below.

In a separate flask, 36 g of tetramethyl orthosilicate (TMOS), 5.44 g of water and 0.5 g of 0.04 M HCl was stirred for about 10 minutes, in order to partially hydrolyze the tetraalkoxide (the hydrolyzed TMOS is called solution 2). To solution 1, 3.5 M HCl was added with rapid stirring in an amount such that the pH was rapidly adjusted to about 6.0 (measured using a pH meter). Immediately after the pH was adjusted to 6.0, the hydrolyzed tetramethyl orthosilicate solution (solution 2) was added to solution 1. The resultant solution gelled within a few seconds. The flask and contents were placed in an over at 80° C. and the material was dried overnight while the oven was purged with nitrogen gas to purge out the volatiles. The dried solid was then dried further under vacuum at 135° C. for 18 hours.

The dried sample was washed by agitation with 3.5 M HCl (100 ml) for 1 hour, filtered and washed with 50 ml of de-ionized water and this acid-washing/water-washing process was repeated five times. After final filtering the material was washed with 500 ml of de-ionized water. The solid was dried under vacuum at 100° C. overnight. The surface area (determined by BET), pore volume and pore diameter was determined to be 529 m$^2$/g, 0.58 cc/g and 3.7 nm respectively.

Using thermogravimetric analysis (TGA), the material showed a weight loss of about 20 wt% between about 450 to 550° C. (due to the loss of organics).

Alkylation of Toluene with n-heptene

Both toluene and n-heptene were dried over 3A molecular sieves before use (dried for 24 hours). In a round bottom flask there were combined 15.6 g of toluene and 8.4 g of n-heptene. A magnetic stirrer coated with fluoropolymer was added. A reflux condenser was attached to the flask and a slow stream of nitrogen passed over the top of the reflux condenser to minimize moisture uptake. The flask and contents were heated to 100° C. A sample of 1 g of the material prepared as in Example 1 was dried in vacuum at 150° C. for 15 hours. The dried material was added to the toluene/n-heptene mixture and the solution stirred and left to react at 100° C. for exactly 2 hours. After two hours a sample was removed and the conversion of n-heptene was measured using gas chromatography (GC). In the GC analysis dodecane was used as an internal standard. The conversion of n-heptene was measured to be >99%, leaving <1% of the heptene unreacted.

Example 2

1 g of $(H_5C_2O)_3Si(CH_2)_3(CF_2)_2O(CF_2)_2SO_2F$ was added to 5 ml of a mixture of distilled water/DMSO/KOH (58% water/30% DMSO/12% KOH) in a sealed vial. The initial mixture of the two immiscible liquids was heated to 90° C. for 18 hours to give a clear solution. The solution was left to cool. The above solution was added dropwise to 5 mL of a 3 M HCl solution with stirring and the pH was measured. The pH changed from <0.1 to about 0.5. NaOH (0.8 M) was then added in an amount to adjust the pH to 1.0, giving a final volume of about 15 ml. This solution was added to 10 g of a Grace 62 porous silica support (available from Grace-Davison) that had been dried overnight at 150° C. under vacuum, and the mixture was vigorously mixed for a few minutes. The flask and contents were heated to 90° C. in an oven for 18 hours and the lid was removed and the solid was left in the oven for a further 18 hours. The solid was finally dried under vacuum at 120° C. for 18 hours.

The solid was stirred with 3.5 M HCl (100 ml) for 1 hour, filtered and washed with distilled, de-ionized water. The process was repeated a total for five times, and after the final filtering the solid was washed with water and redried under vacuum at 100° C.

Alkalation of Toluene with n-heptene

A sample of 1 g of the material prepared as in Example 2 was dried in vacuum at 150° C. for 15 hours. The dried material was added to the toluene/n-heptene mixture and the solution stirred and left to react for exactly 2 hours (as described in Example 1). After two hours a sample was removed and the conversion of n-heptene was measured using GC. In the GC analysis dodecane was used as an internal standard. The conversion of n-heptene was measured to be 60%, leaving 40% of the heptene unreacted.

Example 3

3.5 g of $(H_5C_2O)_3Si(CH_2)_3(CF_2)_2O(CF_2)_2SO_2F$ was added to 15 mL of a mixture of distilled water/DMSO/KOH (58% water/30% DMSO/12% KOH) in a round bottom flask with a reflux condensor attached. The initial mixture of the two immiscible liquids was heated to 90° C. for 18 hours to give a clear solution. The solution was left to cool. This solution will be referred to as solution 1. In a separate flask 34 g of tetramethylorthosilicate, 5.0 g of water and 0.5 g of 0.04 M HCl was stirred for about 10 minutes, which caused hydrolysis of the tetraalkoxide. To solution 1, was added 3.5 M HCl with rapid stirring and the pH was rapidly adjusted to a pH value of about 6.0 (measured using a pH meter). Immediately after the pH was adjusted to 6.0, the hydrolyzed tetramethylorthosilicate solution was added to solution 1 following the pH change to 6.0. The solution gelled within about 1 minute. The flask and contents were placed in an oven at 80° C. and the material was dried overnight while the oven was purged with nitrogen gas to purge out the volatiles. The dried solid was then dried further under vacuum at 135° C. for 18 hours. The dried sample was washed with 3.5 M HCl (100 mL) for 1 hour, filtered and washed with 50 ml of de-ionized water. The acid washing process was repeated a total of five times. After final filtering the material was washed with 500 mL of de-ionized water. The solid was dried under vacuum at 100° C. overnight. The surface area (determined by BET), pore volume and pore diameter was determined to be 830 m²/g, 0.58 cc/g and 2.8 nm respectively. Using thermogravimetric analysis, the material showed a weight loss of about 15 wt % between about 450 to 500° C. (due to the loss of organics).

Alkylation of Toluene with n-heptene

A sample of 1 g of the material prepared as in Example 3 was dried in vacuum at 150° C. for 15 hours. The dried material was added to the toluene/n-heptene mixture and the solution stirred and left to react for exactly 2 hours (as described in Example 1). After two hours a sample was removed and the conversion of n-heptene was measured using GC. In the GC analysis dodecane was used as an internal standard. The conversion of n-heptene was measured to be >99%, leaving <1% of the heptene unreacted.

Example 4

2.6 g of $(H_5C_2O)_3Si(CH_2)_3(CF_2)_2O(CF_2)_2SO_2F$ was added to 40 ml of a mixture of distilled water/DMSO/KOH (58% water/30% DMSO/12% KOH) in a round bottom flask with a reflux condensor attached. The initial mixture of the two immiscible liquids was heated to 90° C. for 18 hours to give a clear solution. The solution was left to cool. This solution will be referred to as solution 1. In a separate flask 68 g of tetramethylorthosilicate, 10.9 g of water and 1 g of 0.04 M HCl was stirred for about 30 minutes, which caused hydrolysis of the alkoxide. To solution 1, was added 3.5 M HCl with rapid stirring and the pH was rapidly adjusted to a pH value of about 6.0 (measured using a pH meter). Immediately after the pH was adjusted to 6.0, the hydrolyzed tetramethylorthosilicate solution was added to solution 1 following the pH change to 6.0. The solution gelled within about 1 minute. The flask and contents were placed in an oven at 80° C. and the material was dried overnight while the oven was purged with nitrogen gas to purge out the volatiles. The dried solid was then dried further under vacuum at 135° C. for 18 hours. The dried sample was washed with 3.5 M HCl (100 mL) for 1 hour, filtered and washed with 50 mL of de-ionized water. The acid washing process was repeated a total of five times. After final filtering the material was washed with 500 ml of de-ionized water. The solid was dried under vacuum at 100° C. overnight. Using TGA, the material showed a weight loss of about 6 wt% between about 450 to 550° C. (due to the loss or organics).

Alkylation of Toluene with n-heptene

A sample of 1 g of the material prepared as in Example 4 was dried in vacuum at 150° C. for 15 hours. The dried material was added to the toluene/n-heptene mixture and the solution stirred and left to react for exactly 2 hours (as described in Example 1). After two hours a sample was removed and the conversion of n-heptene was measured using GC. In the GC analysis dodecane was used as an internal standard. The conversion of n-heptene was measured to be 91%, leaving 9% of the heptene unreacted.

Example 5

1 g of $(H_5C_2O)_3Si(CH_2)_3(CF_2)_2O(CF_2)_2SO_2F$ was added to 7 mL of a mixture of distilled water/DMSO/KOH (58% water/30% DMSO/12% KOH) in a glass vial and the vial was sealed. The initial mixture of the two immiscible liquids was heated at 90° C. for 18 hours to give a clear solution. This solution was added to a stirred solution of sodium silicate (29.9 wt % silica, pH>10). The pH was adjusted to 8 using HCl, after which the solution gelled in a few seconds. The solid was dried in an oven at 100° C. and finally dried overnight in vacuum at 110° C. The dried solid was washed with 3.5 M HCl a total of seven times (approximately 200 mL for each washing). The solid was dried at 100° C. under vacuum.

Acylation of m-xylene with benzoyl chloride m-xylene and benzoyl chloride were dried over a molecular sieve before use. In a round bottom flask was combined 10.6 g of m-xylene and 7 g of benzoyl chloride. A magnetic stirrer coated with fluoropolymer was added. A reflux condensor was attached to the flask and a slow stream of nitrogen passed over the top of the reflux condenser to minimize moisture. The flask and contents were heated to 130° C. A sample of 1 g of the catalyst prepared as described in Example 5 was dried in vacuum at 150° C. for 15 hours. The dried material was added to the m-xylene and benzoyl chloride mixture and the solution was stirred and left to react for exactly 6 hours at 130° C. After six hours a sample was removed. In the GC analysis dodecane was used as a standard. The conversion of benzoyl chloride was found to be 60%.

Example 6

3 g of $(H_5C_2O)_3Si(CH_2)_3(CF_2)_2O(CF_2)_2SO_2F$ was added to 20 ml. of a mixture of distilled water/DMSO/KOH (58% water/30% DMSO/12% KOH) in a round bottom flask with a reflux condenser attached. The initial mixture of the two immiscible liquids was heated at 90° C. for 18 hours to give a clear solution. The solution was left to cool. 7 g of this solution was added to 7 g of a silica support, silica CS-1020E, which is an extrudate purchased from PQ Corporation, Philadelphia, PA. The extrudate and solution were agitated for 10 min. 3 g of 3.5 M HCl was then added to the extrudate containing mixture and the resulting mixture was agitated for an additional hour. The pellets and perfluorosulfonate containing solution were placed in an oven at 110° C. overnight and then dried under vacuum at 110° C. The resulting solid was washed with 500 mL of 3.5 M HCl and stirred for 1 hour. The acid was removed by filtration and the solid was re-suspended in 500 ml of 3.5 M HCl and stirring was continued for a further hour. The solid was washed a total of three times, then finally washed with 500 ml of water, twice. The resulting solid was dried at 100° C. overnight. The solid was then placed in 35% nitric acid and left at 75° C. overnight. The solid was washed with water (500 mL) and then dried at 150° C. for 2 hours.

The solid was found to contain 5.5% of organics (measured by TGA), which were removed in the range of 400–600° C. The ion-exchange capacity determined by titration was found to be 0.18 meq/g and the fluorine analysis was 2.4%.

Alkylation of toluene with n-heptene

A sample of 1 g of the material was dried in vacuum at 150° C. for 15 hours. The dried material was added to the toluene/n-heptene mixture and the solution stirred and left to react for exactly 2 hours (as described in Example 1). After two hours a sample was removed and the conversion of n-heptene was measured using GC. In the GC analysis dodecane was used as a standard. The conversion of n-heptene was measured to be 97%, leaving 3% of the heptene unreacted.

Acylation of m-xylene with benzoyl chloride

The m-xylene and benzoyl chloride were dried over molecular sieve before use. In a round bottom flask was combined 10.6 g of m-xylene and 7 g of benzoyl chloride. A magnetic stirrer coated with fluoropolymer was added. A reflux condenser was attached to the flask and a slow stream of nitrogen passed over the top of the reflux condenser to minimize moisture. The flask and contents were heated to 130° C. A sample of 1 g of the catalyst as described in Example 6 was dried in vacuum at 150° C. for 15 hours. The dried material was added to the m-xylene and benzoyl chloride mixture and the solution was stirred and left to react for exactly 6 hours at 130° C. After six hours a sample was removed. In the GC analysis dodecane was used as a standard. The conversion of benzoyl chloride was found to be 60%.

α-methylstyrene (AMS) dimerization

Catalytic testing of the surface attached composite of Example 6 using the dimerization of AMS was carried out in cumene solvent and comparison was made with "NAFIONO®" catalyst (a registered trademark of E. I. du Pont de Nemours and Company and available in pellet form from Aldrich Chemical Company, prepared from resin of tetrafluoroethylene and perfluoro(3,6-dioxa-4-methyl-7-octene sulfonyl fluoride), "AMBERLYST®"- 15 catalyst (a registered trademark of by Rohm and Haas, Philadelphia, PA and sold by Rohm and Haas). In a 100 ml two neck-flask with magnetic stirring bar was added 5 g AMS, 45 g cumene and 0.5 g solid acid catalyst to be tested which was predried in 150° C. and under vacuum for 15 hours except that the "ANMERLYST®"-15 was dried at 110° C. The reaction temperature was set at 50° C. Liquid samples (0.2 ml each) were taken at 2, 4, 8, 16, 32 and 64 minutes for GC analysis with m-xylene as an internal standard. Three dimers were formed by dimerizing AMS and they are the unsaturated 2,4-diphenyl-4-methyl-1-pentene (I), 2,4-diphenyl-4-methyl-2-pentene (II), and the saturated 1,1,3-trimethyl-3-phenylindan (III). Based on the AMS conversion, the first order rates were calculated and listed in Table 1 below. The product selectivities at ~80% AMS conversion level over different catalysts are listed in Table 2.

TABLE 1

First order rates for the dimerization of α-methylstyrene over solid acid catalysts in organic solvents at ~50° C.

| Catalyst | ($k \sim 10^{-2}$ gmol AMS/gmcatal hr) |
|---|---|
| "NAFION ®" (NR-50) | 0.6 |
| "AMBERLYST ®"-15 | 11.0 |
| Catalyst of present invention | 334.0 |

TABLE 2

Product selectivities (C-mol %) for the dimerization of AMS over solid acid catalysts in cumene at 50° C. and ~80% AMS conversions

| | Product | | |
|---|---|---|---|
| Catalyst | I** | II | III |
| "NAFION ®" (NR-50) | 57.0 | 20.4 | 22.6 |
| "AMBERLYST ®"-15 | 73.9 | 24.3 | 1.7 |
| Catalyst of Present Invention | 88.2 | 9.6 | 2.2 |
| | (93.2)* | (6.1)* | (0.9)* |

*Data obtained at 0° C. and 92.4% AMS conversion
**I is the desired product

Example 7

In this example a modified mesoporous molecular sieve is prepared, based upon a neutral templating route. The basic procedure for making the mesoporous structure (without the fluorocarbon) is described in *Science*, vol. 267, pages 865–867, 1995, by P. T. Tanev and T. J. Pinnavaia.

2.5 of dodecylamine was dissolved in 21 ml of ethanol followed by the addition of 26 ml of water. To this was added simultaneously, 20.4 g of tetraethoxysilane (TEOS) and the following hydrolyzed compound, referred to as solution 1.

Preparation of Solution 1

0.5 g of $(H_5C_2O)_3Si(CH_2)_3(CF_2)_2O(CF_2)_2SO_2F$ was added to 1 ml of a mixture of distilled water/DMSO/KOH (58% water/30% DMSO/12% KOH) in a glass vial and the vial was sealed. The initial mixture of the two immiscible liquids was heated at 90° C. for 18 hours to give a clear solution. The clear solution that resulted is referred to as solution 1.

Solution 1 and the TEOS were added to the dodecylamine/water/ethanol mixture. This mixture was left to stir for 24 hours and the solid was then filtered. The solid was air dried. The template (dodecylamine) was removed with 100 ml of hot ethanol (stirring for 1 hour). The product was filtered and then washed with a second portion of hot ethanol, and the material was finally dried at 100° C. under vacuum. F analysis showed fluorine to be present with a content of 2.1 wt %, F. Powder x-ray diffraction showed a diffraction peak at 2.4 (2 theta) with a d spacing of 3.5 nm.

This example shows the formation of a mesoporous structure which has been modified (in-situ) to incorporate the additional perfluorosulfonate which is chemically bonded to the large pore zeolitic type structure.

Example 8

1 g of $(H_5C_2O)_3Si(CH_2)_3(CF_2)_2O(CF_2)_2SO_2F$ was added to 6 of a mixture of distilled water/DMSO/KOH (58% water/30% DMSO/12% KOH) in a vial and the vial sealed. The initial mixture of the two immiscible liquids was heated at 90° C. for 18 hours to give a clear solution. The solution was left to cool. This solution was added to 7 g of dried silica CS-1020E, and the silica and added solution were mixed for 10 min. To this was added 2.6 g of 3.5 M HCl, well mixed and left at room temperature for 2 hours. The sealed vial was then heated for 2 h at 95° C. The solid was then washed extensively with distilled water (3–4 washes with 1 liter of water). The solid was then dried under vacuum. The solid was washed with 500 nE of 3.5 M HCl and stirred for 1 hour. The acid was removed by filtration and then re-suspended in 500 mL of 3.5 M HCl and stirring was continued for a further hour. The solid was washed a total of three times then finally with water, washed with 500 mL of water, twice. Using TGA, the material showed a weight loss of about 5 wt % between about 450 to 550° C. (due to the loss of organics).

1-Butene Isomerization 1-butene isomerization to cis-2-butene, trans-2-butene and isobutene was carried out at 50–150° C. and ambient pressure with a ½" stainless steel reactor and 2.5 g of the catalyst prepared in Example 8 and 5.0 g "NAFION®" NR50 catalyst, respectively. Prior to the reaction, the catalysts were dried in a vacuum oven at 150° C. for more than 2 hr. The reaction mixtures were analyzed by an on-line GC equipped with a 25 m Plot Column coated with $Al_2O_3/KCl$. The experimental results obtained at the same 1-butene weight hourly space velocity (WHSV) over the catalyst of the present invention and "NAFION®" NR50 catalyst are listed in Table 3a and 3b, respectively. The catalyst of the present invention is very efficient for the 1-butene isomerization under mild conditions. The 1-butene isomerization reached equilibrium at 100° C. over the catalyst of the present invention while even at 150° C. the butene distribution had still not reached the equilibrium values over the "NAFION®" NR50 catalyst. Isobutene was produced only in trace amounts over both catalysts.

TABLE 3a

Product distribution for the 1-butene isomerization over 2.5 g 3% catalyst of the present invention under ambient pressure with flow rates of He = 80 mL/min and 1-butene = 19 mL/min, WHSV of 1-butene = 1 hr$^{-1}$

| % Butenes | Temperature (° C.) | 50 | 100 | 150 |
|---|---|---|---|---|
| 1-butene | | 51.6 | 8.6 | 14.2 |
| t-2-butene | | 23.0 | 62.2 | 54.4 |

TABLE 3a-continued

Product distribution for the 1-butene isomerization over 2.5 g 3% catalyst of the present invention under ambient pressure with flow rates of He = 80 mL/min and 1-butene = 19 mL/min, WHSV of 1-butene = 1 hr$^{-1}$

| % Butenes | Temperature (° C.) | 50 | 100 | 150 |
|---|---|---|---|---|
| c-2-butene | | 25.4 | 29.2 | 31.3 |
| isobutene | | — | — | 0.1 |

TABLE 3b

Product distribution for the 1-butene isomerization over 5.0 g "NAFION" NR-50 catalyst under ambient pressure with flow rate of He = 1-butene = 38 mL/min, WHSV of 1-butene = 1 hr$^{-1}$

| % Butenes | Temperature (° C.) | 50 | 100 | 150 |
|---|---|---|---|---|
| 1-butene | | >99.0 | 86.1 | 38.1 |
| t-2-butene | | — | 5.8 | 36.0 |
| c-2-butene | | <1.0 | 8.0 | 25.7 |
| isobutene | | — | 0.1 | 0.2 |

Example 9

1 g of $(CH_3CH_2O)_3Si(CH_2)_2(CF_2)_2O(CF_2)_2SO_2F$ was added to 6 mL of a mixture of distilled water/DMSO/KOH (58% water/30% DMSO/12% KOH) in a vial and the vial sealed. The initial mixture of the two immiscible liquids was heated at 90° C. for 18 hours to give a clear solution. The solution was left to cool. This solution was added to 7 g of a silica support, silica CS-1020E, which is an extrudate from PG Corporation. The extrudate and solution were agitated for 15 min. using a vortex mixer. 2.8 g of 3.5 M HCl was then added to extrudate and the mixture was left for 2 hours. The pellets and perfluorosulfonate containing solution were placed in an oven at 90° C. overnight and then dried under vacuum at 120° C. The solid was washed with 500 mL of 3.5 M HCl and stirred for 1 hour. The acid was removed by filtration and then re-suspended in 500 mL of 3.5 M HCl and stirring was continued for a further hour. The solid was washed a total of three times then finally with water, washed with 500 ml of water, twice. The solid was dried at 100° C. overnight. The solid was found to contain 3% of organics (measured by TGA), which were removed in the range of 400–550° C.

Alkylation reaction

Catalytic testing of the solid prepared in Example 9 using the alkylation of toluene with n-heptene was carried out. A sample of 1 g of the material was dried in vacuum at 150° C. for 15 hours. The dried material was added to the toluene/n-heptene mixture and the solution stirred and left to react for exactly 2 hours (as described in Example 1). After two hours a sample was removed and the conversion of n-heptene was measured using GC. In the GC analysis dodecane was used as a standard. The conversion of n-heptene was measured to be 82%, leaving 18% of the heptene unreacted.

Example 10

Catalyst for the Polymerization of Tetrahydrofuran

In dry 20 ml, capped vials 5 ml of a solution of 3 vol % of acetic anhydride [0.52 M] and acetic acid [0.32 M] in dry (distilled from sodium) THF [11.59 M] were rotated on mechanical rollers at 25° C. in the presence of 0.494 g of dried catalyst (see Example 9, equiv. wt. =7812) [12.56 mEq/l]. Small samples were withdrawn periodically, quenched with triethylamine, concentrated under nitrogen and dried to constant weight at 60° C./vacuum. These samples were shown by nmr to be essentially free of residual monomer, acetic acid or acetic anhydride. Conversion (gravimetric) increased with time according to zero order kinetics at a constant rate of 12.4%/hr until the limiting equilibrium conversion (61%) was reached. Molecular weights (by gpc in THF using poly tetramnethyleneglycol standards) after 2 hrs.(22.7% conv.) were Mn=33 10, Mw =6360, mol.wt.dist.=1.92 and after 4 hrs. (48.8% conv.) were Mn=2870, Mw=5700, mol.wt.dist.=1.98. By nmr the 4 hr sample had Mn=2710 assuming acetate groups on both ends of the polymer chain as expected for the acetic anhydride chain transfer controlled polymerization. MALDI-TOF mass spectroscopy confirmed that the product was a distribution of polymers predominantly substituted on both ends with acetate groups. In duplicate experiments in which the catalyst was recovered, washed with THF/methanol mixture, dried and reused, the catalytic activity remained essentially constant. At 16.9–17.3 mEq/l catalyst concentration the zero order rate of THF polymerization was 11. 5%/hr for the 1st and the 5th use of the catalyst.

What is claimed is:

1. A compound having the formula $$X_n R^1{}_m SiR^2 R_f SO_2 Y \qquad \text{I}$$

wherein:

X is a hydrolyzable group selected from the group consisting of: halogen, alkoxy, and acyloxy;

each $R^1$ is a non-hydrolyzable group independently selected from the group consisting of: alkyl, cycloalkyl, alkenyl, cycloalkenyl, aryl and aralkyl;

n is an integer from 1 to 3, and in is an integer from 0 to 2, wherein n+m =3;

$R^2$ is a bidentate hydrocarbylene group having at least 2 carbon atoms between Si and $R_f$;

$R_f$ is a substantially fluorinated bidentate hydrocarbylene group; and

Y is fluorine, chlorine or alkoxy.

2. The compound of claim 1 wherein $R_f$ is $CF_2$ or $(CF_2)_2O(CF_2)_2$.

3. The compound of claim 1 wherein Y is F.

4. The compound of claim 1 wherein $R^2$ is $(CH_2)_k$, wherein k is an integer from 2 to 12.

5. The compound of claim 4 wherein k is 2 or 3, and X is ethoxy, n=3, m=0, $R_f$) is $(CF_2)_2O(CF_2)_2$, and Y is F.

6. A compound having the formula $$[(HO)_n R^1{}_m SiR^2 R_f SO_3^-]_x Q^{x+} \qquad \text{II}$$

wherein:

each $R^1$ is a non-hydrolyzable group independently selected from the group consisting of: alkyl, cycloalkyl, alkenyl, cycloalkenyl, aryl and aralkyl;

n is an integer from 1 to 3, and m is an integer from 0 to 2, wherein n+m=3;

$R^2$ is a bidentate hydrocarbylene group having at least 2 carbon atoms between Si and $R_f$;

$R_f$ is a substantially fluorinated bidentate hydrocarbylene group;

Q is H, $NH_4$ or a metal ion, each Q having a valence of x; and x is a number 1 to 4.

7. The compound of claim 6 wherein $R_f$ is $CF_2$ or $(CF_2)_2O(CF_2)_2$.

8. The compound of claim 6 wherein Q is H.

9. The compound of claim 6 wherein $R^2$ is $(CH_2)_k$, wherein k is an integer from 2 to 12.

10. The compound of claim 9 wherein k is 2or 3, n=3, m=0, $R_f$ is $(CF_2)_2O(CF_2)_2$, and Q is K or H.

11. A siloxane or a polysiloxane, comprising: at least two groups, said groups being the same or different, having the formula $$-O)_q(OH)_{n-q}SiR^1{}_m R^2 R_f SO_3 Q,$$

wherein:

each $R^1$ is a non-hydrolyzable group independently selected from the group consisting of: alkyl, cycloalkyl, alkenyl, cycloalkenyl, aryl and aralkyl;

n is an integer from 1 to 3, and m is an integer from 0 to 2, wherein n+m=3;

$R^2$ is a bidentate hydrocarbylene group providing at least 2 carbon atoms between Si and $R_f$;

$R_f$ is a substantially fluorinated bidentate hydrocarbylene group;

Q is H, $NH_4$ or a metal ion, each Q having a valence of x;

x is a number from 1 to 4; and q is l to n.

12. The siloxane or polysiloxane of claim 11 wherein $R_f$ is $CF_2$ or $(CF_2)_2O(CF_2)_2$.

13. The siloxane or polysiloxane of claim 11 wherein Q is H.

14. The siloxane or polysiloxane of claim 11 wherein $R^2$ is $(CH_2)_k$, wherein k is an integer from 2 to 12.

15. The siloxane or polysiloxane of claim 14 wherein k is 2 or 3, n=3, m=0, $R_f$ is $(CF_2)_2O(CF_2)_2$, and Q is K or H.

16. A composite, comprising: a metal oxide network with at least one group having the formula $$-O)_q Si(OH)_{n-q} R^1{}_m R^2 R_f SO_3 Q$$

incorporated within said metal oxide network, wherein:

each $R^1$ is a non-hydrolyzable group independently selected from the group consisting of: alkyl, cycloalkyl, alkenyl, cycloalkenyl, aryl and aralkyl;

n is an integer from 1 to 3, and m is an integer from 0 to 2, wherein n+m=3;

$R^2$ is a bidentate hydrocarbylene group having at least 2 carbon atoms between Si and $R_f$;

$R_f$ is a substantially fluorinated bidentate hydrocarbylene group;

Q is H, $NH_4$ or a metal ion, each Q having a valence of x;

x is a number from 1 to 4; and q is l to n.

17. The composite of claim 16 wherein the metal oxide is silica or alumina.

18. The composite of claim 16 wherein $R_f$ is $CF_2$ or $(CF_2)_2O(CF_2)_2$.

19. The composite of claim 16 wherein Q is H.

20. The composite of claim 16 wherein $R^2$ is $(CH_2)_k$, wherein k is an integer from 2 to 12.

21. The composite of claim 20 wherein k is 2 or 3, n=3, m=0, $R_f$ is $(CF_2)_2O(CF_2)_2$, and Q is K or H.

22. A composition, comprising: a solid material having a reactive surface to which surface is attached at least one group having the formula $-O)_q Si(OH)_{n-q} R^1{}_m R^2 R_f SO_3 Q,$ wherein:
- each $R^1$ is a non-hydrolyzable group independently selected from the group consisting of: alkyl, cycloalkyl, alkenyl, cycloalkenyl, aryl and aralkyl;
- n is an integer from 1 to 3, and m is an integer from 0 to 2, wherein n+m=3;
- $R^2$ is a bidentate hydrocarbylene group having at least 2 carbon atoms between Si and $R_f$;
- $R_f$ is a substantially fluorinated bidentate hydrocarbylene group;
- Q is H, $NH_4$ or a metal ion, each Q having a valence of x;
- x is a number from 1 to 4; and
- q is 1 to n.

23. The composition of claim 22 wherein the metal oxide is silica or alumina.

24. The composition of claim 22 wherein $R_f$ is $CF_2$ or $(CF_2)_2O(CF_2)_2$.

25. The composition of claim 22 wherein Q is H.

26. The composition of claim 22 wherein $R^2$ is $(CH_2)_k$, wherein k is an integer from 2 to 12.

27. The composition of claim 26 wherein k is 2 or 3, n=3, m=0, $R_f$ is $(CF_2)_2O(CF_2)_2$, and Q is K or H.

28. An improved process for the alkylation of an aromatic or substituted aromatic compound with an olefin wherein the improvement comprises contacting said aromatic or substituted aromatic compound with said olefin in the presence of a catalyst comprising the compound of claim 6, the siloxane or polysiloxane of claim 11, the composite of claim 16 or the composition of claim 22.

29. An improved process for the acylation of an aromatic or substituted aromatic compound with an acyl halide wherein the improvement comprises contacting said aromatic or substituted aromatic compound with said acyl halide in the presence of a catalyst comprising the compound of claim 6, the siloxane or polysiloxane of claim 11, the composite of claim 16 or the composition of claim 22.

30. An improved process for the dimerization of an α-substituted styrene wherein the improvement comprises contacting said α-substituted styrene with a catalyst comprising the compound of claim 6, the siloxane or polysiloxane of claim 11, the composite of claim 16 or the composition of claim 22 at a temperature ranging from about −10° C. to about 100° C.

31. An improved process for the isomerization of an olefin wherein the improvement comprises contacting said olefin with a catalyst comprising a compound of claim 6, the siloxane or polysiloxane of claim 11, the composite of claim 16 of composition of claim 22.

32. An improved process for the polymerization of tetrahydrofuran wherein the improvement comprises contacting acetic anhydride, acetic acid and tetrahydrofuran in the presence of a catalyst comprising the compound of claim 6, the siloxane or polysiloxane of claim 11, the composite of claim 16 or the composition of claim 22.

33. A catalyst comprising the compound of claim 6, the siloxane or polysiloxane of claim 11, the composite of claim 16 or the composition of claim 22 in the shape of spherical particles.

34. A process for the regeneration of a catalyst comprising the compound of claim 6, the siloxane or polysiloxane of claim 11, the composite of claim 16 or the composition of claim 22 comprising the steps of:
- contacting a used catalyst with a solution comprising an oxidizing acid and/or an oxidizing agent; and
- washing the catalyst with at least one of: water and an organic solvents.

35. The process of claim 34 further comprising at least one of the following steps: heating the catalyst, isolating the catalyst and drying the catalyst.

* * * * *